United States Patent

Messmer et al.

[11] Patent Number: 4,994,448
[45] Date of Patent: Feb. 19, 1991

[54] CONDENSED QUINOLINIUM AND ISOQUINOLINIUM DERIVATIVES

[75] Inventors: András Messmer; György Hajós; Zsuzsa Juhász née Riedl; Pál Benkó; László Pallos; Lujza Petöcz; Enikö Szirt née Kiszelly; Gábor Gigler; István Gyertyán; Mária Hegedüs, all of Budapest, Hungary

[73] Assignee: Egis Gyogyszergyar, Budapest, Hungary

[21] Appl. No.: 251,445

[22] Filed: Sep. 30, 1988

[30] Foreign Application Priority Data

Oct. 2, 1987 [HU] Hungary ..................... 4436/87

[51] Int. Cl.$^5$ .............. A61K 31/535; C07D 413/04; C07D 417/04; C07D 253/08
[52] U.S. Cl. .......................... 514/227.5; 514/231.5; 514/243; 514/228.5; 544/112; 544/183; 544/60
[58] Field of Search ............. 514/243, 231.5, 227.5, 514/228.5; 544/112, 183, 60

[56] References Cited

U.S. PATENT DOCUMENTS

| | | |
|---|---|---|
| 4,602,018 | 7/1986 | Messmer et al. ............ 544/183 |
| 4,753,938 | 6/1988 | Messmer et al. ............ 544/183 |

FOREIGN PATENT DOCUMENTS

2081261  2/1982  United Kingdom ............ 544/183

OTHER PUBLICATIONS

Kakehi, et al., "Preparation of New Nitrogen-Bridged Heterocycles. Reaction of Pyridinium N-Imines with Azirine Derivatives", *J. Org. Chem.*, vol. 41, No. 16, 1976, 2739-2742.

Kakehi, et al., "Synthesis of 2H-Pyrido[1,2-b]-Triazines Using Azirines Generated by Modified Neber Reactions", *J. Org. Chem.*, vol. 42, No. 14, 1977, 2514-2517.

March, *Advanced Organic Chemistry*, 3rd Ed., pp. 901-902, 1985.

*Primary Examiner*—Mary C. Lee
*Assistant Examiner*—Catherine Scalzo
*Attorney, Agent, or Firm*—Keil & Weinkauf

[57] ABSTRACT

The new compounds of the general Formula I

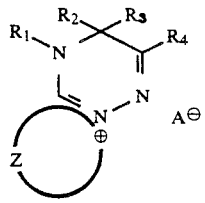

(wherein
$R_1$ stands for $C_{1-4}$ alkyl or aralkyl; and
$R_2$ represents hydroxy; or
$R_1$ and $R_2$ together form a valency bond;
$R_3$ is hydrogen, $C_{1-4}$ alkyl, $C_{1-4}$ alkoxy, phenyl, amino, alkylthio or a group of the Formula —$NR_7R_8$ in which $R_7$ and $R_8$ may be the same or different and stand for hydrogen, $C_{1-4}$ alkyl, phenyl-$C_{1-4}$ alkyl, hydroxy-$C_{1-4}$ alkyl or di-($C_{1-4}$ alkyl)-amino-$C_{1-4}$ alkyl or together with the nitrogen atom they are attached to form a 6-membered heterocyclic ring which may optionally contain a further nitrogen, oxygen or sulfur atom; or
$R_2$ and $R_3$ together form an oxo (=O) or thixo (=S) group;
$R_4$ represents hydrogen, $C_{1-4}$ alkyl or phenyl which may optionally bear one or two halogen or nitro substituent(s);
Z is a group of the Formula (a) or (b)

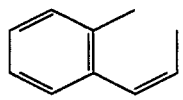 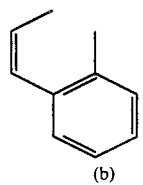

(a)    (b)

and

A$^-$ represents an anion)
and isomers thereof possess useful local anaesthetic, antidepressant, tranquillo-sedative and smooth muscle relaxant properties accompanied by a weaker analgesic effect and are useful in therapy.

3 Claims, No Drawings

CONDENSED QUINOLINIUM AND ISOQUINOLINIUM DERIVATIVES

This invention relates to new condensed quinolinium and isoquinolinium derivatives, a process for the preparation thereof, pharmaceutical compositions comprising the same and also to the use of the said condensed quinolinium and isoquinolinium derivatives for the treatment of diseases and for the preparation of pharmaceutical compositions suitable for the treatment and prophylaxis of the said diseases.

According to an aspect of the present invention there are provided new condensed quinolinium and isoquinolinium derivatives of the general Formula I and isomers thereof (wherein $R_1$ stands for $C_{1-4}$ alkyl or aralkyl; and
$R_2$ represents hydroxy; or
$R_1$ and $R_2$ together form a valency bond;
$R_3$ is hydrogen, $C_{1-4}$ alkyl, $C_{1-4}$ alkoxy, phenyl, amino, alkylthio or a group of the Formula $-NR_7R_6$ in which $R_7$ and $R_8$ may be the same or different and stand for hydrogen, $C_{1-4}$ alkyl, phenyl-$C_{1-4}$ alkyl, hydroxy-$C_{1-4}$ alkyl or di-($C_{1-4}$ alkyl)-amino-$C_{1-4}$ alkyl or together with the nitrogen atom they are attached to form a 6-membered heterocyclic ring which may optionally contain a further nitrogen, oxygen or sulfur atom; or
$R_2$ and $R_3$ together form an oxo (=O) or thioxo (=S) group;
$R_4$ represents hydrogen, $C_{1-4}$ alkyl or phenyl which may optionally bear one or two halogen or nitro substituent(s);
Z is a gorup of the formula (a) or (b)

(a)   (b)

and $A^-$ represents an anion).

The term "lower alkyl" or "$C_{1-4}$ alkyl" used throughout the specification relates to straight or branched chain alkyl groups having 1–4 carbon atoms (e.g. methyl, ethyl, n-propyl, isopropyl, n-butyl etc.). The term "lower alkoxy" or "$C_{1-4}$ alkoxy" relates to alkyl ether groups comprising the above-defined alkyl groups. Under the term "aralkyl group" alkyl groups substituted by one phenyl, substituted phenyl or naphthyl group are to be understood (e.g. benzyl, β-phyenyllethyl etc.). The term "alkylthio" stands for groups as methylthio, ethylthio, n-propylthio etc. As "hydroxyalkyl" groups lower alkyl groups substituted by a hydroxy group are mentioned (e.g. hydroxymethyl, βhydroxyethyl etc.). The "dialkylaminoalkyl" groups comprise lower alkyl groups as defined above (e.g. dimethylaminomethyl, dimethylaminoethyl, dimethylaminopropyl, diethylaminoethyl etc.). The $-NR_7R_8$ heterocyclic group may be e.g. piperidino, morpholino, piperazino, N-methyl-piperazino, N-benzyl-piperazino etc.

$A^-$ may stand for any pharmaceutically acceptable anion, e.g. an anion of an inorganic acid (e.g. hydrosulfide, chloride, bromide, tetrafluoroborate, perchlorate etc.) or an organic acid (e.g. ethanesulfonate etc.). $A^-$ preferably stands for perchorate, chloride or ethanesulfonate.

A preferred class of the compounds of the general Formula I is the compound group in which Z is a group of the Formula (a).

Particularly preferred compounds of the general Formula I are the following derivatives:

2,3-diphenyl-as-triazino[3,2-a]isoquinolinium-chloride;
2-hydroxy-2-methl-1,2-dihydro-as-triazino[3,2-a]isoquinolinium ethanesulfonate;
2-amino-3-phenyl-as-triazino[3,2-a]isoquinolinium ethanesulfonate;
2-methyl-3(4H)-oxo-as-triazino[2,3-a]quinoline-11-ium etanesulfonate;
2-phenyl-3(4H)-oxo-as-triazino[2,3-a]quinoline-11-ium ethanesulfonate;
2-morpholino-as-triazino[3,2-a]isoquinolinium ethanesulfone.

According to a further aspect of the present invention there is provided a process for the preparation of the compounds of the general Formula I and isomers thereof, which comprises (a) for the preparation of heteroaromatic compounds of the general Formula Ia (where $R_3$, $R_4$, Z and $A^-$ are as stated above), reacting a compound of the general Formula IV (where $R_2$ is hydroxy and $R_3$, $R_4$ and Z are as stated above) with an acid of the general Formula VIII $$H-A \qquad \text{(VIII)}$$

(where $A^-$ is as stated above) and, if necessary, with a dehydrating agent; or (b) for the preparation of heteroaromatic compounds of the general Formula Ib

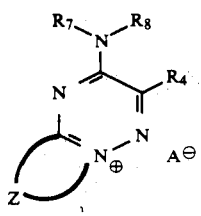

Ib (wherein R4, R7, R8, Z and A⁻ are as stated above), reacting a compound of the general Formula XII

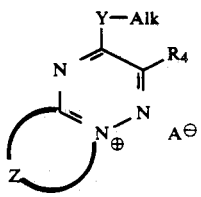

XII (wherein Alk stands for $C_{1-4}$ alkyl, Y is —O— or —S— and R4, Z and A⁻ are as stated above) with an amine of the general Formula IX

IX (where R7 and R8 are as stated above); or (c) for the preparation of the non-aromatic compounds of the general Formula Ic

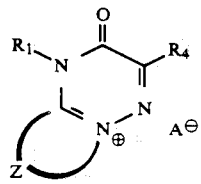

Ic (wherein R1, R4, Z and A⁻ are as stated above), reacting a compound of the general Formula V

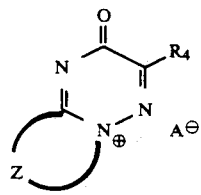

V (wherein R4 and Z are as stated above) with an alkylating or aralkylating agent; and, if desired, replacing in a compound of the general Formula I thus obtained an A⁻ anion for an other A⁻ anion; and/or, if desired, separating a compound of the general Formula I thus obtained into the isomers thereof.

The starting materials of the general Formula IV (wherein R2 stands for hydroxy) used in process (a) are prepared by reacting an amino-isocarbostyrl imine of the general Formula II

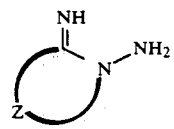

II (wherein Z is as stated above) with a diketone of the general Formula III

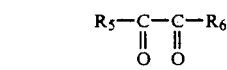

III (wherein R5 and R6 may be the same or different and stand for hydrogen, $C_{1-4}$ alkyl, phenyl or substituted phenyl). The pseudobase of the general Formula IV thus obtained is then reacted with an acid of the general Formula VIII and, if necessary, with a dehydrating agent.

The reaction may be carried out in the absence or presence of an inert organic solvent. As organic solvent halogenated hydrocarbons (e.g. chloroform or chloro benzene), aromatic hydrocarbons (e.g. xylene, toluene, benzene etc.), cyclic ethers (e.g. tetrahydrofurane, dioxane or acetonitrile etc.) may be used. The reaction may be carried out at a temperature between 5° C. and 90° C., preferably at 10°-40° C.

If under the above reaction conditions the compound of the general Formula IV is reacted with a strong acid of the general Formula VIII, the desired compound of the general Formula Ia is directly obtained.

If a compound of the general Formula IV is reacted with a weak acid of the general Formula VIII, a hydroxy compound of the general Formula VII

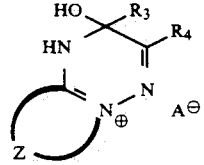

VII is first formed (wherein R3, R4, Z and A⁻ are as stated above) which is then treated with a dehydrating agent. The reaction of the compound of the general Formula VII and the dehydrating agent is accomplished in an anhydrous medium under heating. As dehydrating agent inorganic acid anhydrides (e.g. phosphorous oxychoride, phosphorous pentachloride or polyphosphoric acid) or organic acid anhydrides (e.g. acetic anhydride, propionic anhydrides etc.) may be used.

Water may be split off in an inert organic solvent or in the melt. The excess of the dehydrating agent may also act as reaction medium. As anhydrous inert organic solvent e.g. a halogenated hydrocarbon (e.g. chloroform, dichloro methane, carbon tetrachloride or chloro benzene), aromatic hydrocarbon (e.g. xylene, toluene, benzene), dialkyl amide (e.g. dimethyl formamide), dialkyl sulfoxide (e.g. dimethyl sulfoxide), cyclic ether (e.g. dioxane, tetrahydrofurane), aliphatic ether (e.g. diethyl ether), other hydrocarbons (e.g. n-hexane, petrol) or acetonitrile or a mixture thereof may be used. The reaction may be carried out under heating, preferably at a temperature above 80° C. under atmospheric pressure or in vacuo. If one works in vacuo, the reaction may be accomplished at a lower temperature. The reaction takes some hours.

According to process (b) a compound of the general Formula XII is reacted with an amine of the general Formula IX. It is preferred to use starting materials of the general Formul XII wherein Alk stands for methyl.

The reaction of the compound of the general Formula XII and the amine of the general Formula IX may be carried out in an inert organic solvent. The reaction time varies between half an hour and some hours and takes generally about half an hour or may be even shorter. If compounds of the general Formula XII are used, wherein Y is oxygen (compounds of the general Formula VI

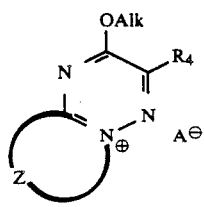

VI wherein Alk, $R_4$, Z and $A^-$ are as stated above), the reaction may be accomplished between room temperature and the boiling point of the solvent, preferably at room temperature. If compounds of the general Formula XII, wherein Y stands for sulfur, are used (compounds of the general Formula XI

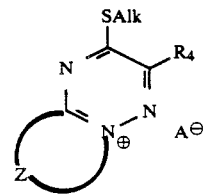

XI wherein Alk, Z, $R_4$ and $A^-$ are as stated above), one may preferably work at elevated temperature in an inert organic solvent.

The starting materials of the general Formula VI may be prepared as follows:

A compound of the general Formula II (wherein Z is as stated above) is reacted with a diacyl compound of the general Formula III (wherein $R_5$ is as stated above and $R_6$ stands for lower alkoxy), whereupon the oxo compound of the general Formula IV [wherein $R_2$ and $R_3$ together form an oxo grop (=O) and $R_4$ and Z are as stated above] thus obtained is treated with an acid of the general Formula VIII (wherein $A^-$ is as stated above), whereupon the compound of the general Formula V (wherein $R_4$, $A^-$ and Z are as stated above) is reacted with an alkylating agent.

The reaction of the pseudobase of the general Formula IV and the acid of the general Formula VIII results in the formation of an -inium salt (isoquinolinium or chinolinium salt, respectively). The reaction may be carried out in the presence or absence of a solvent. As reaction medium it is expedient to use a solvent, in which the acid comprising the $A^-$ anion is soluble and which has a sufficient basicity required to bind the anion. The solvents enumerated in connection with process (a) may be used, preferably polar aprotic solvents (e.g. acetonitrile).

Alkylation of the compound of the general Formula V may be accomplished by using alkylating agents generally applicable for the formation of —OAlkyl compounds. Thus carried out in an inert solvent at an elevated temperature. The reaction takes place within some hours. One may also use alkyl halides (e.g. methyl iodide) as alkylating agent, in acetonitrile, at the boiling point of the solvent.

The starting materials of the general Formula Xi may be prepared as follows:

A compound of the general Formula V is subjected to thionation, whereby a compound of the general Formula X

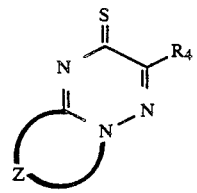

X is obtained (wherein $R_4$ and Z are as stated above) which is the thiono analogue of a pseudobase of the general Formula IV. Thionation is carried out with a suitable sulfide, preferably with a sulfide of a calcogenic element (e.g. phosphorous pentasulfide) at an elevated temperature in basic medium. One may work preferably in pyridine or quinoline as solvent.

The thione of the general Formula X thus obtained is converted into a compound of the general Formula XI (wherein Alk, $R_4$, Z and $A^-$ are as stated above). Alkylation may be accomplished in an analogous manner to that of the compounds of the general Formula V.

According to process (c) a compound of the general Formula V is reacted with an alkylating or aralkylating agent. In this reaction, which leads to the compounds of the general Formula Ic, the alkylating agents and reaction conditions disclosed in connection with the alkylation of the compounds of the general Formula A may be used.

In the course of the above reactions the reaction mixtures obtained are worked up by methods known per se (e.g. evaporation, filtration, extraction, distillation etc.).

In a compound of the general Formula I and $A^-$ anion may be replaced by an other $A^-$ anion by methods known per se. The reaction may be carried out by reacting a compound of the general Formula I with an acid or salt comprising the desired $A^-$ is ethanesulfonate, may be prepared by reacting a compound of the general Formula I comprising an other anion (e.g. perchlorate) with ethanesulfonic acid.

A compound of the general Formula I may be separated into its isomers by methods known per se. are known compounds. The preparation of 1,2-diaminoisoquinolinium tosylate is described in J. Org. Chem. 46, 843 (1981).

The starting materials and intermediates of the general Formulae IV, V, VI, VII, X and XI are new compounds, which can be prepared as disclosed in the present patent specification and the examples.

The compounds of the general Formula I exhibit local anaesthetic, antidepressant, tranquillant/sedative and/or smooth muscle relaxant effects which are accompanied by a weaker analgesic effect.

The activity of the compounds of the general Formula I is shown by the following tests.

1. Acute toxicity on mice

White mice belonging to the CFLP strain (body weight 18–22 g; both male and female) are used, 10 animals for each dose. The test compound is administered orally in a volumen of 20 ml/kg. After treatment the animals are observed for a period of 7 days. The animals are kept in a plastic cage, at room temperature. The animals get tap water and standard mouse fodder ad libitum. The toxicity data are determined with the aid of the method of Litchfield-Wilcoxon and are summarized in Table 1.

TABLE 1

| Acute toxicity on mice | |
| --- | --- |
| Example No. | $LD_{50}$ mg/kg p.o. |
| 16 | 650 |
| 9 | 900 |
| 11 | 2000 |
| 1 | 440 |
| 34 | 1200 |
| 36 | 1400 |
| 5 | 2000 |
| 6 | 850 |
| 8 | 340 |
| 38, 4 | 380 |
| 39 | 500 |
| 40 | 90 |
| 37 | 750 |
| 2 | 450 |
| 3 | 500 |
| 9 | 400 |
| 21 | 700 |
| 17 | 1000 |
| 18 | 2000 |
| 24 | 130 |
| 25 | 500 |
| 26 | 450 |

2. Local anaesthetic effect

Method

The test is carried out by the method of Truant d'Amato. 0.2 ml. of the test compound is injected with a 1 cm. long needle around the nervus ischaidicus, to the center of the femur. The missing motor control of the foot muscles is regarded as a criterium of anaesthesia. The duration of effect is registered and the 50 % effective concentration ($EC_{50}\%$) is calculated on the basis of the dose-effect curve. As reference substance Lidocain is used. The results are summarized in Table 2.

TABLE 2

| Local anaesthetic effect | |
| --- | --- |
| Test compound, Example No. | $EC_{50}$ % concentration |
| 1 | 0.22 |
| 38, 4 | 0.26 |
| 39 | 0.18 |
| 40 | 0.25 |
| 37 | 0.30 |
| 3 | 0.70 |
| 4 | 0.85 |
| 9 | 0.19 |
| 17 | 0.55 |
| Lidocain | 0.21 |

The effective concentration of the compounds of the general Formula I is of the same order of magnitude as that of Lidocain. In the same concentration, however, the majority of the compounds of the general Formula I show a significantly longer effect, the duration of effect being 2.3–5.6 times longer than that of Lidocain.

3. Tetrabenazine antagoniusm on mice

Method

The test is carried out by the method of Hoffmeister et al. adapted to mice. For each does groups of 10 animals are used. The mice of the test groups are treated orally with the test compound while the controld animals receive the corresponding vehicle p.o. After 30 minutes a 50 mg./kg. i.p. dose of Tetrabenazine is administered. The animals with closed eye-lids are counted after 30, 60, 90 and 120 minutes, respectively, in each group.

Evaluation

The average ptosis is calculated on the basis of all measurements in each group and expressed as the percentage of the deviation (ptosis) from the control group. The $ED_{50}$ data are calculated on the basis of these results and the values are summarized in Table 3.

TABLE 3

| Tetrabenazine antagonism on mice | | |
| --- | --- | --- |
| Test compound, Example No. | Tetrabenazine ptosis antagonism $ED_{50}$ mg./kg. | Therapeutical index TI |
| 36 | 20.0 | 70.0 |
| 38, 4 | 9.2 | 41.3 |
| 3 | 50.0 | 10.0 |
| Amitriptylin | 12.0 | 18.7 |

The therapeutical index of the compounds of the general Formula I is significantly higher than that of Amitriptylin.

4. Reserpin ptosis antagonism on mice

Methods

Groups consisting of 10 mice are used for each does. The animals are treated with a 6 mg./kg. s.c. dose of reserpine, the test compound is administered after 60 minutes. The control animals receive a vehicle. The animals with closed eye-lids are counted in each group after 60 and 120 minutes. The evaluation is carried out as disclosed in the ptosis test No. 3. The results are summarized in Table 4.

TABLE 4

| Reserpin ptosis on mice | | |
| --- | --- | --- |
| Test compound, Example No. | Reserpin ptosis antagonism $ED_{50}$ mg./kg. | Therapeutical index TI |
| 11 | 33 | 60.6 |
| 8 | 31 | 11.0 |
| 17 | 40 | 25.0 |
| 18 | 40 | 50.0 |
| Amitriptylin | 65 | 3.5 |

The reserpin inhibiting effect of the compounds of the general Formula I is clearly superior to that of Amitriptylin regarding both the absolute dose and the therapeutical index.

5. Hexobarbital narcosis on mice

Method

Groups consisting of 6 mice are used for each dose. The animals are treated orally with the test compound (the control group receives a vehicle), whereby sleeping is induced 1 hour later by administering a 40 mg./kg. i.v. dose of Hexobarbital both to the test and control groups.

Evaluation

Animals which have a sleeping time more than 2.5 times longer than that of the control group are considered to show a positive reaction. $ED_{50}$ values are calculated from the thus-transofrmed data. The results are summarized in Table 5.

TABLE 5

| Hexobarbital narcosis on mice | | |
|---|---|---|
| Test compound, Example No. | ED$_{50}$ mg./kg. | Therapeutical index |
| 9 | 56 | 16.1 |
| 6 | 35 | 24.3 |
| 38, 4 | 17 | 22.4 |
| Meprobamate | 260 | 4.2 |

The compounds of the general Formula I are superior to the reference substance Meprobamate regarding both the absolute dose and the therapeutical index. The narcosis potentiating effect is accompanied by a weak motility inhibiting effect.

6. Analgesic effect

Method: acetic acid "writhing effect" on mice

To mice weighing 20–25 g. a 0.75% acetic acid solution is administered intraperitoneally in a volume of 20 ml./kg. According to the method of Neubold the characteristic writhing reactions are counted for each animal between the 5th and 10th minute and the total writhing number obtained for this 5 minutes' period is expressed as the percentage of the control group. The test compound is administered orally, the test is carried out by using a pre-treatment period of 60 minutes and 10 animals are used for each dose. The results are summarized in Table 6.

TABLE 6

| Analgesic effect "writhing test" on mice | | |
|---|---|---|
| Test compound, Example No. | ED$_{50}$ mg./kg. | Therapeutical index |
| 27 | 23.8 | 42.0 |
| 9 | 107.3 | 8.4 |
| 1 | 60.0 | 7.3 |
| 6 | 120.0 | 7.1 |
| 38, 4 | 65.0 | 5.8 |
| Paracetamol | 180 | 2.8 |

The compounds of the general Formula I are superior to the reference compound Paracetamol concerning both the absolute dose and the therapeutical index.

7. Effect on the gastrointestinal peristalsis

Method

The antiperistaltic effect is tested according to the method of Stickney et al. on white male and female mice weighing 20–25 g. The test compound is administered at the 60th minute before applying a 10% carbon suspension. The groups consist of 10 mice for each dose. The animals of the control group are treated at the same time under identical conditions with a vehicle. Twenty minutes after the administration of the carbon suspension the mice are sacrificed. The total length of the intestines and that of the intestines filled with carbon is measured. The results are summarized in Table 7.

TABLE 7

| Antiperistaltic effect on mice | | |
|---|---|---|
| Test compound, Example No. | ED$_{50}$ mg./kg. | Therapeutical index |
| 11 | about 220 | 9.1 |
| 40 | 6.5 | 13.85 |
| Papaverin | above 280 mg./kg. ED$_{50}$ can not be determined | 36.1% inhibition |

The new condensed as-triazine derivatives differ also qualitatively from known compounds of similar structure. The compounds of the general Formula I are practically void of antiarrhythmial, spasmolytic and antitremorine effect, while a part of these new compounds exhibit a significant narcosis potentiating and weaker motility inhibiting activity. The new compounds of the present invention show a more specific effect. The compounds of the general Formula I can be characterized by an antidepressant effect with a sedative effect component or only by a tranquillant-sedative, local anaesthetic and weaker analgesic effect. The most potent spasmolytic compound exerts significant antianginal effect as well.

According to a further aspect of the present invention there are provided pharmaceutical compositions comprising as active ingredient at least one compound of the general Formula I or an isomer thereof in admixture with suitable inert solid or liquid pharmaceutical carriers. The pharmaceutical compositions of the present invention can be prepared by methods known per se by admixing the active ingredient with suitable inert solid or lqiuid carriers and bringing the mixture to galenic form.

The pharmaceutical compositions of the present invention may be suitable for oral (e.g. tablet, pill, coated pill, capsule, solution, emulsion, suspension), rectal (e.g. suppository) or parenteral (e.g. injectable solution) administration. The pharmaceutical compositions contain conventional solid or liquid carriers (e.g. starch, magnesium stearate, calcium carbonate, talc, lactose etc.). The pharmaceutical compositions may also contain generally used auxiliary agents and/or excipients (e.g. disintegrating, suspending, emulsifying and wetting agents, buffers, salts for adjusting the osmotic pressure etc.) and optionally further therapeutically active compounds.

The daily dosage of the compounds of the general Formula I can vary between wide ranges and amounts preferably to 0.3–10 mg./kg./day in case of peroral administration and to 0.05–4 mg./kg./day incase of parenteral administration.

We wish to note that the above values are but of informative character and the actual dose always depends on the circumstances of the given case (efficiency of the active ingredient used, route of application, condition and age of the patient, severeness of the disease etc.) and is determined by the physician.

According to a further aspect of the invention there is provided the use of compounds of the general Formula I or an isomer thereof for the preparation of pharmaceutical compositions having local anaesthetic, antidepressant, tranquillant/sedative and smooth muscle relaxant effect.

According to a still further aspect of the present invention there is provided a method of local anaesthetic, antidepressant, tranquillant/sedative and smooth muscle relaxant treatment which comprises administering to the patient an effective amount of a compound of the general Formula I (wherein R$_1$, R$_2$, R$_3$, R$_4$, Z and A$^-$ are as stated above) or an isomer thereof.

Further details of the present invention are to be found in the following Examples without limiting the scope of protection to the said Examples.

EXAMPLE 1

2,3-Dimethyl-2-hydroxy-1,2-dihydro-as-triazino[3,2-a]isoquinolinium ethanesulfonate To a solution of 0.6 g. (0.0026 mole) of 2,3-dimethyl-2-hydroxy-1,2-dihydro-as-triazino[3,2-a]isoquinoline and 5 ml of acetonitrile 0.29 g. of ethanesulfonic acid is added at 40° C. whereupon the solution is stirred for an hour, then cooled. The precipitated crystals are filtered and washed with ether. Thus 0.4 g. of the desired compound is obtained, yield 46%, mp.: 75°-78° C.

The starting material is prepared as follows:

To 1.0 g (0.003 mole) of 1,2-diamino-isoquinolinium tosylate 3 ml. of a 5% sodium hydroxide solution are added and the suspension formed is stirred at 25° C. for 30 minutes. For a transitory period a solution is formed but later a solid product precipitates which is filtered. Thus 0.39 g. of 2-amino-isocarbostyrylimine are obtained, yield 81%, mp.: 79°-81° C.

0.8 g (0.005 mole) of the product thus obtained is admixed with 20 ml. of methanol, whereupon at room temperature 0.5 mole of diacetyl are added. The reaction mixture is stirred for an hour, the preicpitated product is filtered and dried in vacuo. Thus 0.7 g. of 2,3-dimethyl-2hydroxy-2,5-dihydro-as-triazino[3,2-a]isoquinoline is obtained, yield 2%, mp.: 69°-71° C.

EXAMPLE 2

2-Morpholino-as-triazino[3,2-a]isoquinolinium ethanesulfonate

A solution of 10 g (0.0027 mole) of the starting material disclosed in paragraph (c) of this example (perchlorate salt) and 170 ml. of ethyl acetate is admixed under warming with a solution of 15 g. of tetrabutyl ammonium ethanesulfonate in ethyl acetate, whereupon the reaction mixture is cooled. The precipitated white product is filtered. Thus 8.2 g of the desired compound are obtained, yield 80%, mp.: 186°-187° C.

The starting material is prepared as follows (from 2-amino-isocarbostyryl imine):

(a) as-Triazino[3,2-a]isoquinoline-2(5H)-one 15.9 g (0.1 mole) of 2-amino-isocarbostyryl imine are reacted with 12.4 g (0.12 mole) of ethyl glyoxylate in 100 ml. of methanol at room temperature. The reaction mixture is cooled in an ice bath, the precipitated product is filtered. Thus 16.5 g of the desired compound are obtained, yield 84%, mp.: 226° C.

(b0  2-Methoxy-as-triazino[3,2-a]isoquinolinium perchlorate

A mixture of 19.7 g (0.1 mole) of the product prepared according to paragraph (a) and 150 ml. of dimethyl sulfate is heated at 120°-130° C. for 4 hours under stirring. The dimethyl sulfate is then distilled off in vacuo and to the residue 100 ml. of water and 20 ml. of 70% perchloric acid are added. The precipitated crystalline product is filtered and washed with water. Thus 26.4 g of the desired compound are obtained, yield 85%, mp.: 198°-199° C.

(c) 2-Morpholino-as-triazino[3,2-a]isoquinolinium perchlorate 13.3 g (0.043 mole) of the product prepared according to paragraph (c) are dissolved in 70 ml. of acetonitrile, whereupon under cooling 7.8 ml. of morpholine are added. The reaction mixture is cooled with icecold water and the precipitated product is filtered. Thus 15.5 g. of the desired compound are obtained, yield 94%, mp.: 253°-254° C.

EXAMPLE 3

2-(2-Hydroxyethylamino)-as-triazino[3,2-a]isoquinolinium ethanesulfonate 8.7 g. (0.038 mole) of 2-(2-hydroxyethylimino)-2,5-dihydro-as-triazino[3,2-a]isoquinoline are reacted with 3.13 g. of ethanesulfonic acid in 60 ml. of acetonitrile. After half an hour the reaction mixture is cooled, the precipitated white product is filtered. Thus 8.4 g. of the desired compound are obtained, yield 62%, mp.: 162°-163° C.

In an analogous manner the following compounds are prepared:

2-(2-hydroxyethylamino)-3-methyl-as-triazino[3,2-a]isoquinolinium ethanesulfonate, yield 80%, mp.: 180°-181° C.;

2-(2-hydroxyethylamino)-3-phenyl-as-triazino[3,2-a]isoquinolinium ethanesulfonate, yield 82%, mp.: 161-162° C.

The starting material is prepared as follows:

13.3 g (0.45 mole) of 2-methoxy-as-triazino[3.2-a]isoquinolinium perchlorate are dissolved in 70 ml. of acetonitrile and reacted with 5.32 g. of ethanol amine under cooling for 2 hours. The precipitated yellow product is filtered. Thus 8.7 g. of 2-(2-hydroxyethylimino)-2,5-dihydro-as-triazino[3,2-a]isoquinoline are obtained, yield 85%, mp.: 185°-186° C.

In an analogous manner the following compounds are prepared:

2-(2-hydroxyethylimino)-3-methyl-2,5-dihydro-as-triazino[3,2-a]isoquinoline. Yield 90%, mp.: 143°-144° C.

2-(2-hydroxyethylimino)-3-phenyl-2,5-dihydro-as-triazino[3,2-a]isoquinoline, yield 85%, mp.: 141°-142° C.

EXAMPLE 4

2-Amino-as-triazino[3,2-a]isoquinolinium ethanesulfonate.

A solution of 5.8 g. (0.03 mole) of 2-imino-2,5-dihydro-as-triazino[3,2-a]isoquinoline and 40 ml of acetonitrile is admixed with 2.44 g. of ethanesulfonic acid. The reaction mixture is stirred for half an hour, then cooled. The precipitate is filtered and recrystallized from acetonitrile. Thus 7.2 g. of the desired compound are obtained, yield 78%, mp.: 216°-217° C.

In an analogous manner the following compounds are prepared:

2-amino-3-methyl-as-triazino[3,2-a]isoquinolinium ethanesulfonate, yield 80%, mp.: 221'-222° C.;

2-amino-3-phenyl-as-triazino[3,2-a]isoquinolinium ethanesulfonate, yield 85%, mp.: 214°-215° C.

The starting material is prepared as follows:

A solution of 13.3 g (0.045 mole) of 2-methoxy-as-triazino[3,2-a]isoquinolinium perchlorate and 70 ml. of acetonitrile is reacted with 4.4 ml. of a 25% ammonium hydroxide solution in the cold for 2 hours. The precipitated yellow product is filtered. Thus 5.8 g. of 2-imino-2,5-dihydro-as-triazino[3,2-a]isoquinoline are obtained, yield 67%, mp.: 120°-121° C.

In an analogous manner the following compounds are prepared:

2-imino-3-methyl-2,5-dihydro-as-triazino[3,2-a]isoquinoline, yield 76%, mp.: 168°-169° C.;

2-imino-3-phenyl-2,5-dihydro-as-triazino[3,2-a]isoquinoline, yield 72%, mp.: 166°-167° C.

EXAMPLE 5

2-(3-Dimethylaminopropylamino)-3-methyl-as-triazino[3,2-a]isoquinolinium ethanesulfonate One proceeds according to Example 3 except that 2-(3-dimethylaminopropylimino)-3-methyl-2,5-dihydro-as-triazino[3,2-a]isoquinoline is used as starting material, yield 69%, mp.: 136°-137° C.

EXAMPLE 6

2-(3-Dimethylaminopropylamino)-3-phenyl-as-triazino[3,2-a]isoquinolinium ethanesulfonate One proceeds according to Example 3 except that 2-(3-dimethyliminopropyl-imino)-3-phenyl-2,5-dihydro-as-triazino[3,2-a]isoquinoline is used as starting material, yield 75%, mp.:194°–195° C.

EXAMPLE 7

2-Benzylamino-3-methyl-as-triazino[3,2-a]isoquinolinium ethanesulfonate

One proceeds according to Example 3 except that 2-benzylimino-3-methyl-2,5-dihydro-as-triazino[3,2-a]isoquinoline is used as starting material, yield 85%, mp.: 145°–146° C.

EXAMPLE 8

2-Benzylamino-3-phenyl-as-triazino[3,2-a]isoquinolinium ethanesulfonate

One proceeds according to Example 3 except that 2-benzylimino-3-phenyl-2,5-dihydro-as-triazino[3,2-a]isoquinolinine is used as starting amterial, yield 22%, mp.: 123°–124° C.

EXAMPLE 9

3-Methyl-2(1H)-oxo-as-triazino[3,2-a]isoquinolinium-5-ium-ethanesulfonate 8.2 g. (0.04 mole) of 3-methyl-as-triazino[3,2-a]isoquinoline-2(5)-one are reacted with 4.4 g. (0.04 mole) of ethanesulfonic acid in 50 ml. acetonitrile. The precipitation of the crystalline product is enhanced by the addition of ether. Thus 11.6 g. of the desired compound are obtained, yield 90%, mp.: 131°–132° C.

The starting material is prepared as follows:

A solution of 15.0 g. (0.094 mole) of 1-amino-isocarbostyryl-imine and 100 ml. of methanol is reacted with 12.4 ml. (0.11 mole) of ethyl pyruvate. The reaction mixture is cooled on an ice-bath, the precipitated product is filtered and washed with cold acetonitrile. Thus 8.8 g. of 3-methyl-as-triazino[3,2-a]isoquinoline-2-(5H)-one are obtained, yield 44%, mp.: 206°–208° C.

EXAMPLE 10

2-Methoxy-3-methyl-as-triazino[3,2-a]isoquinolinium hexafulorophosphate

A solution of 0.21 g. (0.001 mole) of 3-methyl-as-triazino[3,2-a]isoquinoline-2(5H)-one and 5 ml. of anhydrous dichloromethane is admixed with 0.21 g. of trimethyl oxonium-hexafluorphophsate, then the reaction mixture is stirred at room temperature until a solution is formed. The mixture is stirred overnight, the precipitated crystalline product is filtered. Thus 0.35 g. of the desired compound are obtained, yield 94%, mp.: 190°–191° C.

EXAMPLE 11

3-Phenyl-as-triazino[3,2-a]isoquinoline-2(5H)-one

To a solution of 9.0 g. (0.0057 mole) of 2-amino-isocarbostyryl imine and 80 ml. of methanol 12.1 g. (0.068 mole) of phenyl glyoxylic acid ethyl ester are added, the reaction mixture is stirred, then cooled in an ice-bath and the precipitated product is filtered. Thus 11.2 g. of the desired compound are obtained, yield 72%, mp.: 240°–241° C.

EXAMPLE 12

2,3-Diphenyl-as-triazino[3,2-a]isoquinolinium tetrafluoroborate

A mixture of 0.4 g. (0.0012 mole) of 1,2-diamino-isoquinolinium tosylate, 0.27 g. (0.0013 mole) of dibenzoyl and 5 ml of concentrated sulfuric acid is stirred for 3 hours. The reaction mixture is poured on ice and fluoroboric acid is added. The precipitated product is filtered. Thus 0.36 g. of the desired compound are obtained, yield 72%, mp.: 266°–267° C.

EXAMPLE 7

2,3-Dimethyl-as-triazino[3,2-a]isoquinolinium perchlorate 7.7 g. (0.048 mole) of 2-amino-isocarbostyryl imine are dissolved in 190 ml of dichlormethane, whereupon 5.37 ml. (0.0623 mole) of diacetyl are added under strong cooling. The precipitated product is filtered, suspended in acetonitrile and 7 ml. of 70% perchloric acid are added. The product is precipitated by adding ether. Thus 9.18 g. of the desired compound are obtained, yield 61%, mp.: 211°–212° C.

EXAMPLE 14

2,3-Dimethyl-as-triazino[3,2-a]isoquinolinium hydrogensulfate 9.5 g. (0.033 mole) of 2,3-dimethyl-as-triazino[3,2-a]isoquinolinium perchlorate are subjected to anion-exchange in acetonitrile at room temperature by using 26 g. of tetrabutyl ammonium hydrogen sulfate. Thus 9.1 g. of the desired compound are obtained, yield 96.5% mp.: 190° C. (decomposition).

In analogous manner the following compound is prepared:

3-phenyl-as-triazino[3,2-a]isoquinolinium bromide, yield 66%, mp.: 235° C.

EXAMPLE 15

2-Hydroxy-3-(p-chorophenyl)1,2-dihydroas-triazino[3,2-a]isoquinolinium ethanesulfonate 11.6 g. (0.0374 mole) of 2-hydroxy-3-(p-chlorophenyl) 2,5)dihydro-as-triazino[3,2-a]isoquinoline are converted into the ethanesulfonate salt in an analogous manner to Example 1. Yield 90%, mp.: 129°–130° C.

The starting material is prepared in an analogous manner to Example 1 by using 2-amino-isocarbostyryl imine and p-chloro-phenyl glyoxylic acid. Yield 70%, mp.: 780°–71° C.

EXAMPLE 16

2-Hydroxy-1,2-dihydro-as-triazino[3,2-a]isoquinolinium ethanesulfonate

One proceeds in an analogous manner to Example 1 by using 4.2 g (0.021 mole) of 2-hydroxy-2,5-dihydro-as-triazino[3,2-a]isoquinoline as starting material. Thus 5.8 g. of the desired compound are obtained, yield 95%, mp.: 144°–145° C.

EXAMPLE 17

2,4-Dimethyl-3(4H)-oxo-as-triazino[3,2-a]isoquinoline-11-ium ethanesulfonate

A solution of 10 g. (0.03 mole) of 2,4-dimethyl-3(4H)-oxo-as-triazino[3,2-a]isoquinoline-11-ium perchlorate and 20 ml. of acetonitrile is reacted with a solution of 16 g. of tetrabutyl ammonium ethanesulfonate formed with ethyl acetate. Thus in the form of white crystals 7.2 g. of the desired compound are obtained, yield 71%, mp.: 156°–157° C.

The starting material is prepared as follows:

To a suspension of 8.7 g. (0.041 mole) of 2-methyl-as-triazino[3,2-a]quinoline-3(11H)-one and acetonitrile 30 ml. of dimethyl sulfate are added. The reaction mixture is heated to boiling for 5 hours, the solvent is evaporated, the residue is diluted with water and 9 ml. of 70% perchloric acid are added. In the form of white crystals 10.2 g. of 2,4-dimethyl-3(4H)- oxo-as-triazino[3,2-a]quinoline-11-ium perchlorate are obtained, yield 76%, mp.: 190°–192° C.

EXAMPLE 18

2-Phenyl-4-methyl-3(4H)-oxo-as-triazino[3,2-a]quinoline-11-ium ethanesulfonate

One proceeds in an analogous manner to Example 17 except that 2-phenyl-as-triazino[3,2-a]quinoline-3-(11H)-one is used as starting material. The desired compound is obtained with a yield of 83%, mp.: 204°–205° C.

The 2-phenyl-4-methyl-3(4H)-oxo-as-triazino[3,2-a]quinoline-11-ium-fluoroborate used as starting material is obtained with a yield of 72%, mp.: 298°–299° C.

EXAMPLE 19 as-triazino[3,2-a]quinolinium ethanesulfonate 5.6 g (0.027 mole) of as-triazino[3,2-a]quinoline are reacted with 2.23 ml. of ethanesulfonic acid in acetonitril. From the yellow solution formed the desired compound is precipitated by adding ether. Yield 7.6 g. (95%); mp.: 135°–136° C.

The starting material is prepared as follows:

5.4 g (0.034 mole) of 1-amino-carbostyryl imine are stirred with 6.3 ml. (0.037 mole) of 30% glyoxale. Thus in the form of white crystals 5.6 g. of as-triazino[3,2-a]quinoline are obtained, yield 81%, mp.: 113°–114° C.

EXAMPLE 20

2-Methyl-as-triazino[3,2-a]quinolinium ethanesulfonate

To a solution of 6.5 g. (0.0306 mole) of 2-methyl-3-hydroxy-3,11-dihydro-as-triazino[3,2-a]quinoline in acetonitrile 2.51 ml. of ethanesulfonic acid are added. The reaction having been completed ether is added and the solution is cooled in an icebath. Thus 5 g. of the crystalline desired compound are obtained, yield 54%, mp.: 145°–146° C.

The starting material is prepared as follows:

A solution of 8 g. (0.05 mole) of 1-amino-carbostyryl imine in acetonitrile is reacted with a 40% aqueous solution of 9.4 ml. (0.058 mole) of methyl glyoxale. On standing white crystals precipitate from the soltuion which are filtered. The reaction mixture is allowed to stand and cooled with an ice-bath. In the form of white crystals 6.5 g. of 2-methyl-3-hydroxy-3,11-dihydro-as-triazino[3,2-a]quinoline are obtained, yield 61%, mp.: 152°–153° C. (decomposition).

EXAMPLE 21

2-Methyl-3(4H)-oxo-as-triazino[3,2-a]quinoline-11-ium ethanesulfonate

To a solution of 1.05 g (0.005 mole) of 2-methyl-as-triazino[3,2-a]quinoline-3(11H)-one 5 ml. of acetonitrile 0.5 ml. of ethanesulfonic acid are added. From the solution formed white crystals precipitate. Thus 1.4 g. of the desired compound are obtained, yield 86%, mp.: 171°–172° C.

The starting material is prepared as follows: 2.18 g. (0.002 mole) of 1-amino-carbostyryl imine are dissolved in 20 ml. of acetonitrile, whereupon 2.6 ml. (0.0024 mole) of ethyl pyruvate are added dropwise under stirring. A thick precipitate falls out. The reaction mixture is allowed to stand for half an hour, then cooled with an ice-bath and filtered. Thus 2.22 g. of 2-methyl-as-triazino[3,2-a]quinoline-3(11H)-one are obtained, yield 53%, mp.: 242°–244° C.

EXAMPLE 22

Alternative process for the preparation of the starting material of the compound of Example 17

0.21 g (0.001 mole) of 2-methyl-as-triazino[3,2-a]quinoline-3(11H)-one is dissolved in 6 ml. of acetonitrile, whereupon 1.0 ml. of methyl iodide are added dropwise. The reaction mixture is heated to boiling for an hour. The yellow solution formed is heated to a further period of 3 hours to boiling. The precipitation of crystals begins. Thus 0.3 g. of 2,4-dimethyl-3(4H)-oxo-as-triazino[3,2-a]quinolin-11-ium-iodide are obtained, yield 86%, mp.: 248°–249° C.

EXAMPLE 23

2-Phenyl-as-triazino[3,2-a]quinolinium perchlorate 2.0 g (0.00126 mole) of 1-amino-carbostyryl-imine are dissolved in 50 ml. of acetonitrile, whereupon 1.9 g. (0.00126 mole) of phenyl glyoxale mononydrate are added under stirring. A precipitate falls out whereupon the reaction mixture is stirred for 20 hours and 1 ml. of 70% perchloric acid is added. The precipitate goes into solution and falls out on the addition of ether. Thus 2.5 g. of the desired compound are obtained, yield 57%, mp.: 247°–248° C.

EXAMPLE 24

2-Methyl-3(2-hydroxyethylamino)as-triazino[3,2-a]quinolinium ethanesulfonate 6.5 g. (0.0025 mole) of 2-methyl-3-(2-hydroxyethylimino)-3,11-dihydro-as-triazino[3,2-a]quinoline are suspended in 50 ml. acetonitrile, whereupon 2.1 ml. of ethane-sulfonic acid are added. The desired compound precipitates soon in the form of white crystals, yield 7.2 g (79%), mp.: 184°–185° C.

The starting material is prepared as follows:

To a suspension of 10 g. (0.0028 mole) of 2-methyl-3-(2-hydroxyethylamino)as-triazino[3,2-a]quinolinium perchlorate and 20 ml. of ethanol 10 ml. of a 20% sodium hydroxide solution are added. The precipitated yellow crystals are filtered and recrystallized from dimethyl formamide. Thus 6.9 g. op 2-methyl-3-(2-hydroxyethylimino)-3,11-dihydro-as-triazino[3,2-a]quinoline are obtained, yield 96%, mp.: 211°–212° C.

EXAMPLE 25

3-(2-Hydroxyethylamino)-2-phenyl-as-triazino[3,2-a]quinolinium ethanesulfonate

To a solution of 7.0 g. (0.0022 mole) of 3-(2-hydroxyethylimino)-2-phenyl-3,11-dihydro-as-triazino[3,2-a]quinoline and acetonitrile 1.8 ml. of ethanesulfonic acid are added. The desired compound precipitates in the form of white crystals, yield 7.8 g. (83%), mp.: 181°–182° C.

The starting material is prepared as follows:

To a suspension of 10.4 g. (0.0025 mole) of 3-(2-hydroxyethylamino)-2-phenyl-as-triazino[3,2-a]quinolinium perchlorate and 40 ml. of ethanol 10 ml. of a 20% sodium hydroxide solution are added. The product goes into solution, whereafter yellow crystals precipitate. Thus 7.2 g. of 3-(2-hydroxyethylimino)-2-phenyl-3,11-dihydro-as-triazino[3,2-a]quinoline are obtained, yield 91%, mp.: 172°–174° C.

EXAMPLE 26

3(4H)-Oxo-as-triazino[3,2-a]quinoline-11ium ethanesulfonate

To a suspension of 4.5 g. (0.0023 mole) of as-triazino[3,2-a]quinoline-3(11H)-one and acetonitrile 1.88 ml. of ethanesulfonic acid are added dropwise and from the solution white crystals precipitate. Thus 6.7 g. of the desired compound are obtained, yield 95%, mp.: 180°–181° C.

The starting material is prepared as follows:

15.9 g. (0.01 mole) of 1-amino-carbostyryl-imine are dissolved in 100 ml. of acetonitrile, whereupon 12.4 g. (0.012 mole) of ethyl glyoxylate are added dropwise; a white precipitate appears. The reaction mixture is cooled on an ice-bath for an hour, whereupon the precipitated produt is filtered. Thus 12.6 g. of as-triazino[3,2-a]quinoline-3(11H)-one are obtained, yield 65%, mp.: 191°–192° C.

EXAMPLE 27

2-Phenyl-3(4H)-oxo-as-triazino[3,2-a]quinoline-11ium ethanesulfonate

To a mixture of 9.5 g. (0.035 mole) of 2-phenyl-as-triazino[3,2-a]quinoline-3(11H)-one and 50 ml. of ethanol 2.9 ml. of ethanesulfonic acid are added under stirring. From the solution formed the desired product is precipitated by adding ether. Thus 11.2 g. of the desired compound are obtained, yield 84%, mp.: 145°–146° C.

The starting material is prepared as follows:

9.0 g. (0.0057 mole) of 1-amino-carbostyryl imine are suspended in 80 ml. of acetonitrile, whereupon 12.1 g. (0.00581 mole) of phenyl glyoxylic acid ethyl ester are added dropwise under stirring. After temporary dissolving a precipitate appears. The mixture is cooled on an ice-bath for half an hour. The precipitated product is filtered. Thus 9.6 g. of 2-phenyl-as-triazino[3,2-a]quinoline-3(11H)-one are obtained, yield 60%, mp: 232°–233° C.

EXAMPLE 28

2,3-Dimethyl-as-triazino[3,2-a]quinolinium hydrosulfate

A solution of 5.0 g. (0.0061 mole) of 2,3-dimethyl-as-triazino[3,2-a]quinolinium perchorate in acetonitrile is admixed with a solution of 13.7 g. (0.04 mole) of tetrabutyl hydrogen sulfate and 40 ml. of acetonitrile whereby a yellow precipitate appears. The reaction mixture is stirred for an hour and a half. The precipitated product is filtered. Thus 3.0 g. of the desired compound are obtained, yield 60%, mp.: 166°–167° C.

EXAMPLE 29

2,3-Dimethyl-as-triazino[3,2-a]quinolinium perchlorate

To a solution of 10.0 g. (0.0628 mole) of 1-amino-carbostyryl imine in acetonitrile 7 ml. (0.0806 mole) of diacetyl are added under stirring. A yellowish-white precipitate appears. The reaction mixture is stirred for half an hour, whereupon 8 ml. of 70% perchloric acid are added. The desired product is precipitated by adding ether. Yield 11.1 g. 57%, Mp.: 210°–211° C.

The starting material is prepared as follows:

1.0 g. (0.0029 mole) of 1,2-diamino-quinolinium tosylate are admixed with 5 ml. of a 5% sodium hydroxide solution. From the temproarily formed solution a crystalline product precipitates. Thus 0.4 g. of 1-aminocarbostyryl-imine are obtained, yield 85%, mp.: 78°–79° C.

EXAMPLE 30

3-Morpholino-as-triazino[3,2-a]quinolinium perchlorate

To a suspension of 3.3 g. (0.01 mole) of 3-methylthio-as-triazino[3,2-a]quinolinium perchlorate formed with acetonitrile 1.8 ml. of morpholine are added dropwise. The solution is stirred for an hour. The precipitated crystals are filtered. Thus 2.8 g. of the desired compound are obtained, yield 79%, mp.: 207°–208° C.

The starting material is prepared as follows:

To a suspension of 10.0 g. (0.05 mole) of as-triazino[3,2-a]quinoline-3(11H)-one in pyridine 14 g. of phosphorous pentasulfide are added. The reaction mixture is stirred at 60° C. for an hour, then poured into water. The precipitated crystals are filtered. Thus 8.3 g. of as-triazino[3,2-a]quinoline-3(11H)-thione are obtained, yield 78%, mp.: 261°–262° C.

(b) 7.5 g. (0.035 mole) of as-triazino[3,2-a]quinoline-3(11H)-thione are suspended in 70 ml. of acetonitrile, whereupon 7 ml. of dimethyl sulfate are added dropwise. The reaction mixture is heated to boiling for 12 hours, then evaporated. The residue is dissolved in 40 ml. of water, and 7.5 ml. of 70% perchloric acid are added. Thus 10.9 g. of 3-methylthio-as-triazino[3,2-a]quinolinium-perchlorate are obtained, yield 95%, mp.: 244°–245° C.

EXAMPLE 31

3-Morpholino-as-triazino[3,2-a]quinolinium-ethane sulfonate 1.7 g. (0.05 mole) of 3-morphoino-as-triazino[3,2-a]quinolinium perchlorate are admixed with acetonitrile, whereupon a solution of 2 g. of tetrabutyl ammonium ethanesulfonate in ethyl acetate is added. From the solution the precipitation of crystals soon begins. Thus 1.4 g. of the desired compound are obtained, yield 75%, mp.: 191°–193° C.

EXAMPLE 32

3-(2-Hydroxyethylamino)-as-triazino[3,2-a]quinolinium ethanesulfonate

To a suspension of 5.7 g. (0.024 mole) of 3-(2-hydroxyethylimino)-3,11-dihydro-as-triazino[3,2-a]quinoline formed with acetonitrile 2.0 ml. of ethanesulfonic acid are added. In the form of white crystals 7.2 g. of the desired compound are obtained, yield 86%, mp.: 155°–156° C.

The staring material is prepared as follows:

(a) 9.8 g. (0.03 mole) of 3-methylthio-as-triazino[3,2-a]quinolinium perchlorate are suspended in acetonitrile whereupon 3.6 ml. of ethyl amine are added dropwise. From the solution thus formed the precipitation of crystals soon beings. The reaction mixture is stirred for an hour, whereupon ethyl acetate is added and the mixture is filtered. Thus 8.8 g. of 3-(2-hydroxyethylamino)-astriazino[3,2-a]quinolinium perchlorate are obtained, yield 83%, mp.: 173°-174° C.

(b) 8.6 g. (0.025 mole) of the product prepared according to paragraph (a) are admixed with ethanol, whereupon 20 ml. of a 10% sodium hydroxide solution are added. In the form of a yellow crystalline produt 5.7 g. of 3-(2-hydroxyethylimino)-3,11-dihydro-as-triazino[3,2-a]quinoline are obtained, yield 95%, mp.: 115°-116° C.

EXAMPLE 33

3-Amino-as-triazino[3,2-a]quinoline ethanesulfonate 1 g. (0.005 mole) of 3-imino-3,11-dihydro-as-triazino[3,2-a]quinoline are admixed with 10 ml. of acetonitrile, whereupon 0.8 ml. of ethanesulfohnic acid are added. On addition of ethyl acetate the desired product precipitates. Yield 1.2 g. (82%), mp.: 249°-250° C.

The starting material is prepared as follows:

(a) 3.3 g. (0.01 mole) of 3-methylthio-as-triazino[3,2-a]quinolinium perchlorate are admixed with 1 ml. of a concentrated ammonium hydroxide solution in acetonitrile. The solution formed is stirred at room temperature fo an hour, whereby a product precipitates. Thus 2.4 g. of 3-amino-as-triazino[3,2-a]quinolinium perchlorate are obtained, yield 81%, mp.: 257°-258° C.

(b) 1.5 g. of (0.005 mole) of the product prepared according to the previous paragraph are dissolved in 20 ml. of ethanol, whereupon 20 ml. of a 10% sodium hydroxide solution are added. The crystalline precipitate is filtered. Thus 0.8 g. of 3-imino-3,11-dihydro-as-triazino[3,2-a]quinoline are obtained, yield 81%, mp.: 16°-107° C.

EXAMPLE 34

2-Morpholino-3-methyl-as-triazino[3,2-a]isoquinolinium ethanesulfonate

The desired compound is prepared from 2-morpholino-3-methyl-as-triazino[3,2-a]isoquinolinium perchlorate, in an analogous manner to Example 2. Yield 75%, mp.: 156°-157° C.

EXAMPLE 35

2-Morpholino-3-phenyl-as-triazino[3,2-a]isoquinolinium perchlorate

The desired compound is prepared in an analogous manner to Example 2c from 2-methoxy-3-phenyl-as-triazino[3,2-a]isoquinolinium perchlorate. Yield 65%, mp.: 277°-278° C.

EXAMPLE 36

2-(2-Hydroxyethylamino)-3-methyl-as-triazino[3,2-a]isoquinolinium ethanesulfonate The desired compound is prepared from 3-methyl-2-(2-hydroxyethylimino0-2,5-dihydro-as-triazino[3,2-a]isoquinoline in an analogous manner to Example 3. Yield 80%, mp.: 179°-180° C.

EXAMPLE 37

2-(2-Hydroxyethylamino)-3-phenyl-as-triazino[3,2-a]isoquinolinium ethanesulfonate The desired compound is prepared from 2-(2-hydroxyethylimino)-3-phenyl-2,5-dihydro-as-triazino[3,2-a]isoquinoline in an analogous manner to Example 3. Yield 76%, mp.: 214°-215° C.

EXAMPLE 38

2-Amino-3-methyl-as-triazino[3,2-a]isoquinolinium ethanesulfonate

The desired compound is prepared from 2-imino-3-methyl-2,5-dihydro-as-triazino[3,2-a]isoquinoline in an analogous manner to Example 4. Yield 82%, mp.: 222°-223° c.

EXAMPLE 39

2-Amino-3-phenyl-as-triazino[3,2-a]isoquinolinium ethanesulfonate

The desired compound is prepared from 2-imino-3-phenyl-2,5-dihydro-as-triazino[3,2-a]isoquinoline in an analogous manner to Example 3. Yield 87%, mp.: 214°-215° C.

EXAMPLE 40

2-Benzylamino-3-methyl-as-triazino[3,2-a]isoquinolinium ethanesulfonate

The desired compound is prepared form 2-benzylimino-3-methyl-2,5-dihydro-as-triazino[3,2-a]isoquinoline in an analogous manner to Example 3. Yield 90%, mp: 145°-146° C.

EXAMPLE 41

2-Methyl-3-methylthio-as-triazino[3,2-a]quinolinium perchlorate

The desired compound is prepared from 2-methyl-as-triazino[3,2-a]quinoline-3(11H)-thione in an analogous manner to Example 30b. Yield 94%, mp.: 219°-220° C.

EXAMPLE 42

2-Phenyl-3-methylthio-as-triazino[3,2-a]quinolinium perchlorate

The desired compound is prepared from 2-phenyl-as-triazino[3,2-a]quinoline-3(11H)-thione in an analogous manner to Example 30b. Yield 90%, mp.: 251°-252° C.

EXAMPLE 43

2-Methyl-3-morpholino-as-triazino[3,2-a]quinolinium perchlorate

The desired compound is prepared from 2-methyl-3-methylthio-as-triazino[3,2-a]quinolinium perchlorate in an analogous manner to Example 30. Yield 91%, mp.: 238°-239° C.

EXAMPLE 44

2-Phenyl-3-morpholino-as-triazino[3,2-a]quinolinium perchlorate

The desired compound is prepared from 2-ophenyl-3-methylthio-as-triazino[3,2-a]quinolinium perchlorate in an analogous manner to Example 30. Yield 84%, mp.: 285°-286° c.

EXAMPLE 45

2-Methyl-3-(3-dimethylaminopropylamino)-as-triazino[3,2-a]quinolinium perchlorate The desired compound is prepared from 2-methyl-3-(3-dimethylaminopropylimino)-as-triazino[3,2-a]quinoline in an analogous manner to Example 6. Yield 87%, mp.: 183°-184° C.

EXAMPLE 46

2-Phenyl-3-(3-dimethylaminopropylamino)-as-triazino[3,2-a]quinolinium perchlorate The desired compound is prepared from 2-phenyl-3-(3-dimethylamino-propylimino)-as-triazino[3,2-a]quinoline in an analogous manner to Example 6. Yield 82%, mp.: 172°–173° C.

EXAMPLE 47

2-Methyl-3-benzylamino-as-triazino[3,2-a]quinolinium perchlorate

The desired compound is prepared from 2-methyl-3-benzylimino-as-triazino[3,2-a]quinoline in an analogous manner to Example 3. Yield 79%, mp.: 241°–242° C.

EXAMPLE 48

2-Phenyl-3-benzylamino-as-triazino[3,2-a]quinolinium pechlorate

The desired compound is prepared from 2-phenyl-3-benzylimino-as-triazino[3,2-a]quinoline in an analogous manner to Example 3. Yield 84%, mp.: 179°–180° C.

EXAMPLE 49

3-Amino-2-methyl-as-triazino[3,2-a]quinolinium perchlorate

The desired compound is prepared from 3-imino-2-methyl-3,5-dihydro-as-triazino[3,2-a]quinoline in an analogous manner to Example 4. Yield 82%.

EXAMPLE 50

3-Amino-2-phenyl-as-triazino[3,2-a]quinolinium perchlorate

The desired compound is prepared from 3-imino-2-phenyl-3,5-dihydro-as-triazino[3,2-a]quinoline in an analogous manner to Example 4. Yield 92%.

EXAMPLE 51

2-Methoxy-as-triazino[3,2-a]isoquinolinium perchorate

A suspension of 19.7 g. (0.1 mole) of as-triazino[3,2-a]isoquinoline-2(5H)-one and 150 ml of dimethyl sulfate is stirred at 120°–130° C. for 4 hours, whereupon the dimethyl sulfate is distilled off. The residue is admixed with water and 20 ml. of 70% perchloric acid are added. The precipitated crystals are filtered. Thus 26.4 g. of the desired compound are obtained, yield 89%, mp.: 198°–199° C.

What we claim is:

1. A method of providing local anesthesia which comprises administering to a patient in need thereof an anesthetic-effective amount of a compound of the formula:

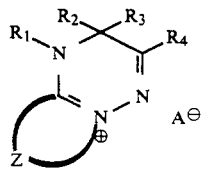

wherein:
$R_1$ is $C_{1-4}$ alkyl or $C_{1-4}$ alkyl substituted by phenyl or naphthyl; $R_2$ is hydroxy; or $R_1$ and $R_2$ together from a valency bond;

$R_3$ is hydrogen, $C_{1-4}$ alkyl, $C_{1-4}$ alkoxy, phenyl, amino, alkylthio or a group of the formula $-NR_7R_8$ in which $R_7$ and $R_8$ may be the same or different and stand for hydrogen, $C_{1-4}$ alkyl, phenyl-$C_{1-4}$ alkyl, hydroxy-$C_{1-4}$ alkyl or di-($C_{1-4}$ alkyl)-amino-$C_{1-4}$ alkyl or together with the nitrogen atom they are attached to form a 6-membered heterocyclic ring which may optionally contain a further nitrogen, oxygen or sulfur atom in the 4 position; or $R_2$ and $R_3$ together form an oxo (=O) or thioxo (=S) group;

$R_4$ represents hydrogen, $C_{1-4}$ alkyl or phenyl which may optionally bear one or two halogen or nitro substituent(s);

Z is a group of the formula (a) or (b)

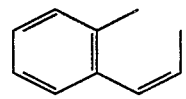    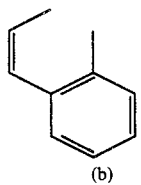

(a)    (b)

and $A^-$ represents an anion.

2. A method of providing sedative activity which comprises administering to a patient in need thereof a sedative-effective amount of a compound of the formula:

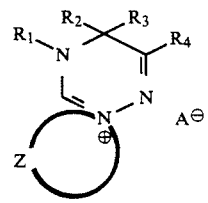

wherein:
$R_1$ is $C_{1-4}$ alkyl or $C_{1-4}$ alkyl substituted by phenyl or naphthyl;

$R_2$ is hydroxy; or $R_1$ and $R_2$ together form a valency bond;

$R_3$ is hydrogen, $C_{1-4}$ alkyl, $C_{1-4}$ alkoxy, phenyl amino, alkylthio or a group of the formula $-NR_7R_8$ in which $R_7$ and $R_8$ may be the same or different and stand for hydrogen, $C_{1-4}$ alkyl, phenyl-$C_{1-4}$ alkyl, hydroxy-$C_{1-4}$ alkyl or di-($C_{1-4}$ alkyl)-amino-$C_{1-4}$ alkyl or together with the nitrogen atom they are attached to form a 6-membered heterocyclic ring which may optionally contain a further nitrogen, oxygen or sulfur atom in the 4 position; or $R_2$ and $R_3$ together form an oxo (=O) or thioxo (=S) group;

$R_4$ represents hydrogen, $C_{1-4}$ alkyl or phenyl which may optionally bear one or two halogen or nitro substituent(s);

Z is a group of the formula (a) or (b)

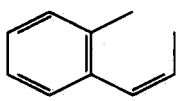
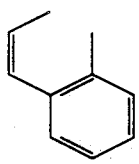

(a)    (b)

and

A⁻ represents an anion.

3. A method of producing a smooth-muscle relaxant effect which comprises administering to a patient in need thereof a smooth-muscle-relaxing-effective amount of a compound of the formula:

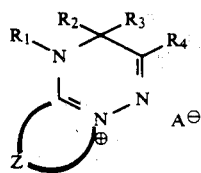

wherein:

$R_1$ is $C_{1-4}$ alkyl or $C_{1-4}$ alkyl substituted by phenyl or naphthyl;

$R_2$ is hydroxy; or $R_1$ an $R_2$ together form a valency bond;

$R_3$ is hydrogen, $C_{1-4}$ alkyl, $C_{1-4}$ alkoxy, phenyl, amino, alkylthio or a group of the formula —$NR_7R_8$ in which $R_7$ and $R_8$ may be the same or different and stand for hydrogen, $C_{1-4}$ alkyl, phenyl-$C_{1-4}$ alkyl, hydroxy-$C_{1-4}$ alkyl or di-($C_{1-4}$ alkyl)-amino-$C_{1-4}$ alkyl or together with the nitrogen atom they are attached to form a 6-membered heterocyclic ring which may optionally contain a further nitrogen, oxygen or sulfur atom in the 4 position; or $R_2$ and $R_3$ together form an oxo (=O) or thioxo (=S) grup;

$R_4$ represents hydrogen, $C_{1-4}$ alkyl or phenyl which may optionally bear one or two halogen or nitro substituent(s);

Z is a group of the formula (a) or (b)

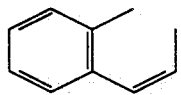
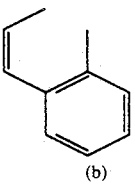

(a)    (b)

and

A⁻ represents an anion.

* * * * *